(12) United States Patent
Shin et al.

(10) Patent No.: US 7,901,916 B2
(45) Date of Patent: Mar. 8, 2011

(54) METHOD FOR PRODUCING HYDROGEN FROM ORGANIC WASTES

(75) Inventors: Hang-Sik Shin, Daejeon (KR);
Dong-Hoon Kim, Daejeon (KR);
Sang-Hyoun Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 820 days.

(21) Appl. No.: 11/798,336

(22) Filed: May 11, 2007

(65) Prior Publication Data
US 2008/0277337 A1 Nov. 13, 2008

(51) Int. Cl.
*C12P 3/00* (2006.01)
(52) U.S. Cl. ........................................ 435/168
(58) Field of Classification Search ................ None
See application file for complete search history.

(56) References Cited

U.S. PATENT DOCUMENTS 6,942,998 B1 * 9/2005 Ooteghem .............. 435/168
2007/0207531 A1 * 9/2007 Ferchichi et al. ......... 435/168

OTHER PUBLICATIONS

Hawkes, F.R. et al., "Sustainable fermentative hydrogen production: challenges for process optimisation," *Int. J. Hydrogen Energ.* 27:1339-1347 (2002), Elsevier Science Ltd.
Jones, D.T. and Woods, D.R., "Acetone-Butanol Fermentation Revisited," *Microbiol. Rev.* 50:484-524 (1986), American Society for Microbiology.
Kim, D.-H. et al., "A Novel Biological Fermentation Process for Hydrogen Production from Food Waste," International Symposium and Poster Presentation (Oct. 20, 2006), Korea Advanced Institute of Science and Technology, pp. 164-170.

Kim, D.-H. et al., Proceedings of the 2006 Spring Conference of the Korea Society of Waste Management (May 12, 2006 first posting date), pp. 8-11.
Kim, S.-H. et al., "Feasibility of biohydrogen production by anaerobic co-digestion of food waste and sewage sludge," *Int. J. Hydrogen Energ.* 29:1607-1616 (2004), Elsevier Ltd.
Lay, J.-J. et al., "Feasibility of Biological Hydrogen Production From Organic Fraction of Municipal Solid Waste," *Wat. Res.* 33:2579-2586 (1999), Elsevier Science Ltd.
Momirlan, M. and Veziroglu, T.N., "Current status of hydrogen energy," *Renew. Sust. Energ. Rev.* 6:141-179 (2002), Elsevier Science Ltd.
Noike, T. et al., "Inhibition of hydrogen fermentation of organic wastes by lactic acid bacteria," *Int. J. Hydrogen Energ.* 27:1367-1371 (2002), Elsevier Science Ltd.
Non-verified, English-language abstract from the Autumn 2006 Symposium featuring Kim, D.-H. et al., "A Novel Biological Fermentation Process for Hydrogen Production from Food Waste" (Oct. 20, 2006).
Non-verified, English-language abstract from the conference materials from the Proceedings of the 2006 Spring Conference of the Korea Society of Waste Management, May 12, 2006 (first posting date).
Okamoto, M. et al., "Biological hydrogen potential of materials characteristic of the organic fraction of municipal solid wastes," *Wat. Sci. Technol.* 41:25-32 (2000), Pergamon Press, Inc.
Shin, H.-S. and Youn, J.-H., "Conversion of food waste into hydrogen by thermophilic acidogenesis," *Biodegradation* 16:33-44 (2005), Kluwer Academic Publishers.

* cited by examiner

*Primary Examiner* — Herbert J. Lilling
(74) *Attorney, Agent, or Firm* — Sterne, Kessler, Goldstein & Fox P.L.L.C.

(57) ABSTRACT

The present invention relates to a method for producing hydrogen by batch process capable of replacing the existing complex continuous organic waste treatment system by using pretreated organic waste not only as a substrate but also an inoculum. According to the present invention, the existing complex continuous process can be changed into a simple batch process, thereby reducing the installment costs and operational costs. It is possible to obtain economic operation because a long initial start-up period is not required.

13 Claims, 7 Drawing Sheets

METHOD FOR PRODUCING HYDROGEN FROM ORGANIC WASTES

BACKGROUND OF THE INVENTION

1. Field of the Invention

The present invention relates, generally to methods for producing hydrogen from organic waste and more particularly to a new hydrogen fermentation batch process capable of replacing the existing complex continuous waste treatment system by using the pretreated organic waste not only as a substrate but also an inoculum.

2. Background Art

Distribution issues and limited supplies of fossil fuels have caused political and diplomatic problems as well as economic problems due to the rise of oil prices. In addition, $CO_2$, $NO_x$ and $SO_x$ emission from burning fossil fuel is now accelerating global warming.

Research for developing alternative energy has increased and is essential for the development of the next generation, especially for countries like Korea that are highly dependent on imported fossil fuels.

Hydrogen is recognized as a remarkable energy source because it generates only water under combustion and therefore displays environment-friendly characteristics. In addition, it has the highest energy content per unit weight of any known fuel and can easily be converted to electric energy via fuel cell technology (see Momirlan, M. and Veziroglu, T. N. Renew. Sust. Energ. Rev., vol. 6, 2002, p. 141-179).

Currently, more than 90% of hydrogen is produced by the water reforming method, however this method uses fossil fuels and is intensive in energy consumption. On the other hand, the method of biological hydrogen production has not been well researched but is recognized as a latent technology in light of the fact that the material costs and energy consumption can be minimized.

The technology of producing hydrogen through anaerobic fermentation is estimated to be practicable technology in comparison to other biological methods because of advantages such as high hydrogen production rate, no use of light energy, and direct use of organic waste for substrate (see Hawkes et al., Int. J. Hydrogen Energ., vol. 27, 2002, p. 1339-1347).

In 2004, food waste accounted for 32.6% of the entire municipal waste in Korea causing a plurality of leachate and stench due to the high portion of volatile solids (85% to 90%) and water content (75% to 85%), thereby raising many problems in the treatment process. Food waste has mainly been treated by landfill, incineration and recycling but the recycling ratio is increasing because landfill has been prohibited since 2005. However, the optimum recycling plan is not yet established.

The majority of sewage sludge is an organic sludge with more than 40% being of organic content. Its production reaches 2.3 million tons every year and 70% of the sewage sludge is dumped to the sea and the rest are treated by incineration, recycling and landfill (based on figures from 2004). However, as regulations for emitting the waste to the sea were strengthened with the action of the London Convention ("96 agreement"), a method to treat sewage sludge on land is urgent.

As such, an anaerobic fermentation technology which degrades organic waste and simultaneously recovers hydrogen, itself a clean energy source, can provide a new alternative. Especially, as it is reported that when food waste is mixed with the sewage sludge to be digested, relatively deficient nutrients in the food waste are provided from the sewage sludge so that the digestion efficiency and the biogas production rate are increased (see Kim et al., Int. J. Hydrogen Energ., vol. 9. 29, 2004, p. 1607-1616).

Much research with regard to hydrogen fermentation of organic waste is in progress. Substrate pretreatments such as heat, acid, and alkali treatment improved hydrogen production by killing the non-hydrogen producing bacteria present in the substrate and increasing hydrolysis. Various kinds of waste were tested for the hydrogen production and technologies for continuous hydrogen production via process control were developed.

However, even if a pretreated substrate was used, when hydrogen is produced from the real waste in continuous operation, limitations were reported, for example, a long start-up period and hydraulic retention time were required and the hydrogen production sometimes fluctuated unstably (see Kim et al., Int. J. Hydrogen Energ., Vol. 27, 2004, p. 1607-1616; Shin and Youn, Biodegradation, Vol. 16, 2005, p. 33-44).

The major reason to improve the performance by controlling process configuration like sequencing batch reactor (SBR) or up flow anaerobic sludge blanket (UASB) in the existing anaerobic digestion process is to maintain the high concentration of microorganisms with good activity and obtain biogas from the organic components in a short time. It is especially effective when methane producing microorganisms are used which have a very slow growth rate.

However, the microorganisms with rapid growth rates like hydrogen producing bacteria showed low hydrogen conversion efficiency at long retention time by competing with the non-hydrogen producing bacteria and an unstable yield was observed in continuous operation. On the contrary, if higher hydrogen yield could be obtained by batch operation, the advantages of the continuous operation would be greatly diminished for hydrogen fermentation. In hydrogen fermentation using food waste as a substrate, the batch operation showed higher hydrogen yield in comparison with continuous operation. Although batch operation showed a lag period of 5 to 20 hours, hydrogen fermentation completed within 1 to 5 days. In case of continuous operation, the optimum hydraulic retention time was about 1.5 to 6 days, which did not show increased efficiency over batch operation (see Lay et al., Wat. Res., vol. 33(11), 1999, p. 2579-2586; Okamoto et al., Wat. Sci. Technol., vol. 41(3), 2000, p. 25-32).

Nevertheless, the batch process has a critical defect, as it is necessary to prepare an inoculum each time, hence the process is cumbersome and a pollutant addition itself.

BRIEF SUMMARY OF THE INVENTION

The present invention is therefore directed to a method for producing hydrogen via a batch process capable of replacing the existing complex continuous organic waste treatment system by using pretreated organic waste not only as a substrate but also an inoculum.

In order to achieve this objective the present invention provides a method for producing hydrogen from organic waste, comprising; (a) pretreating organic waste and (b) fermenting the pretreated organic waste anaerobically, wherein the organic waste is a substrate and an inoculum.

The organic waste used as a substrate in the present invention can be, but is not limited to, food waste, sewage sludge and livestock waste.

The food waste includes various microorganisms such as lactic acid bacteria, propionic acid bacteria, fungi, colon bacillus and the like and is easily corrupted at room temperature. For the above reason, physical and chemical shocks were applied in order to kill the non-hydrogen producing bacteria present in the food waste when used as a substrate (see Noike et al., Int. J. Hydrogen Energ., 27, 2002, p 1367-1371). *Clostridium* sp., known as major hydrogen producing bacteria, are representative of endospore forming bacteria and are present in food. Thus, there is a possibility that food waste pretreatment could achieve two things simultaneously, killing of non-hydrogen producing bacteria and selection of hydrogen producing bacteria.

The pretreatment can be a heat-treatment, an acid treatment, an alkali treatment or a combination thereof. In some embodiments the heat-treatment is performed at about 80° C. to about 100° C. for about 10 minutes to about 30 minutes. In some embodiments the heat treatment is performed at about 85° C. to about 95° C. for about 15 minutes to about 25 minutes. In some embodiments the acid treatment is performed at pH 0.1 to pH 2 for about 12 hours to about 36 hours, and in some embodiments at pH 0.5 to pH 1.5 for about 18 hours to about 30 hours. In some embodiments the alkali treatment is performed at pH 12 to pH 14 and in some embodiments at pH 12.5 to pH 13.5 for about 18 hours to about 30 hours.

The present invention is directed to an anaerobic fermentation that is proceeded by a batch operation method wherein the initial substrate concentration is in some embodiments about 25 g to about 35 g Carbo. COD/L, (Chemical oxygen demand) and in some embodiments about 28 g to about 32 g Carbo. COD/L wherein the initial pH is controlled at pH 7.5 to pH 8.5 and in some embodiments to pH 7.8 to pH 8.2 and thereby it is possible to maximize hydrogen production. Moreover, the cultivation pH of the anaerobic fermentation in some embodiments is controlled from pH 5.6 to pH 6.4 and in some embodiments from pH 5.8 to pH 6.2 and the cultivation temperature in some embodiments is 33° C. to 37° C. and in some embodiments at 34° C. to 36° C.

In the present invention, sewage sludge, a nutrient-rich waste is added to the food waste as a supplementary substrate and therefore it is not only possible to treat a sewage sludge having low biodegradability but also to reduce the entire reaction time, resulting in decreasing the size of reactor for hydrogen fermentation.

According to the present invention, the pretreated sewage sludge is added by about 1% to about 20% (v/v) and in some embodiments by about 5% to about 15% (v/v) of the volume of the entire reactor. In some embodiments it is profitable that the heat treatment is performed at 80° C. to 100° C. for about 10 minutes to about 30 minutes and in some embodiments at 85° C. to 95° C. for about 15 minutes to about 25 minutes.

As mentioned above, in the present invention organic waste, such as food waste is used as a hydrogen fermentation inoculum as well as a substrate and it is possible to produce hydrogen by effectively proceeding to anaerobic fermentation without injecting additional hydrogen producing inoculum.

BRIEF DESCRIPTION OF THE DRAWINGS/FIGURES

DETAILED DESCRIPTION OF THE INVENTION

Figure 1:
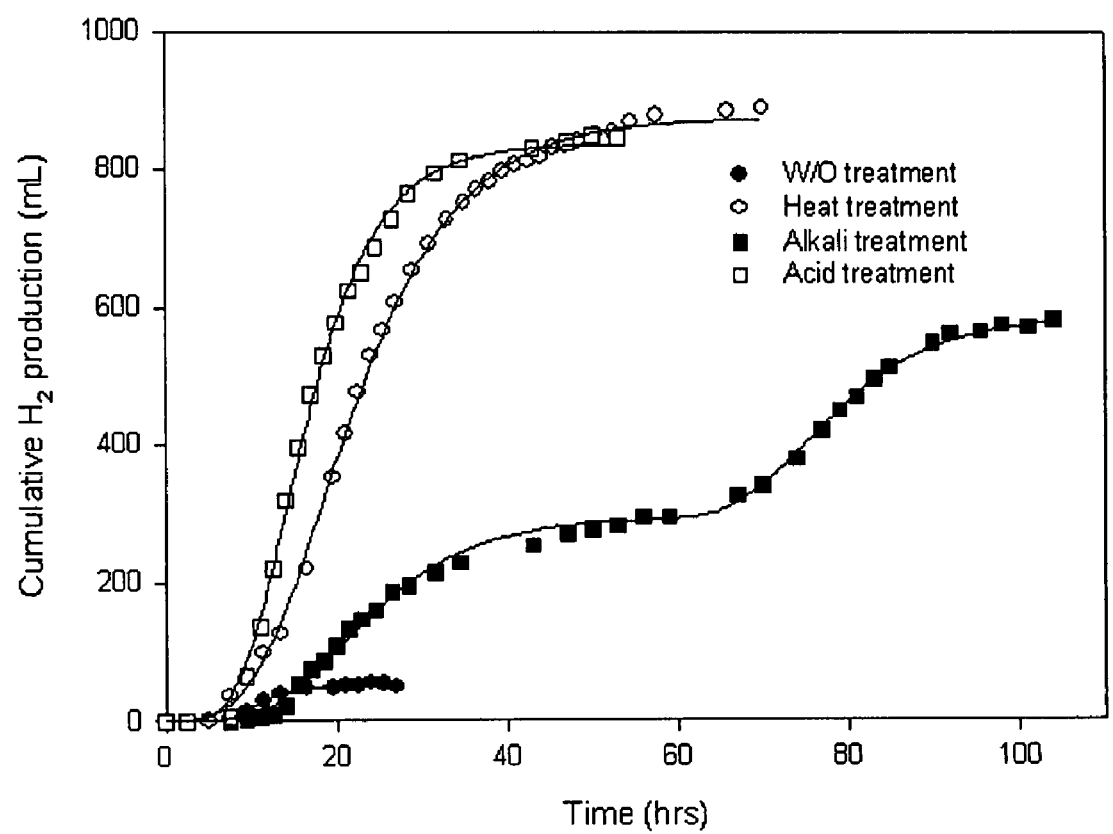
FIG. 1 is a graph showing the cumulative hydrogen production with time under various pretreatment conditions (heat treatment, alkali treatment and acid treatment)

The present invention is directed to a method for producing hydrogen from organic waste, comprising: pretreating organic waste; and fermenting the pretreated organic waste anaerobically, wherein the pretreated organic waste is a substrate and an inoculum. The organic waste can include, but is not limited to, food waste, sewage sludge, livestock waste and combinations thereof. The pretreatment can include, but is not limited to, heat treatment, an acid treatment, an alkali treatment and combinations thereof.

In some embodiments the heat treatment is for about 10 minutes to about 30 minutes at about 80° C. to about 100° C. In some embodiments the acid treatment is for about 12 hours to about 36 hours at pH 0.1 to 2. In some embodiments the alkali treatment is for about 12 hours to about 14 hours at about pH 12 to about pH 14. In some embodiments the anaerobic fermentation is operated by batch process. In some embodiments the method of anaerobic fermentation has a concentration of an initial organic substrate of about 25 g to about 35 g Carbo. COD/L. In some embodiments the anaerobic fermentation has an initial pH of about pH 7.5 to about pH 8.5. In some embodiments the anaerobic fermentation occurs at a cultivation pH of about pH 5.6 to about pH 6.4. In some embodiments the anaerobic fermentation occurs at a cultivation temperature of about 33° C. to about 37° C. In some embodiments the method for producing hydrogen of the present invention further comprises adding a heat-treated sewage sludge to the pretreated organic waste as a supplemental substrate.

In some embodiments the heat-treated sewage sludge is added by about 1% (v/v) to about 20% (v/v) of the volume of the entire reactor. In some further embodiments the heat-treated sewage sludge is heated for about 10 minutes to about 30 minutes at about 80° C. to about 100° C.

EXAMPLES

A better understanding of the present invention can be obtained in light of the following examples which are set forth to illustrate, but are not to be construed to limit the present invention.

Example 1

The food waste used as a substrate for the production of hydrogen in Example 1 was collected from the restaurant of the Korea Advanced Institute of Science and Technology and grinded into less than 5 mm by a crusher.

The used food waste properties included a ratio of carbohydrate to the overall COD (Chemical oxygen demand) of 47.3%, the ratio of COD to TKN (total Kjeldahl nitrogen) was 24:7, and the pH was 5.4. The low pH was due to existence of organic acids such as lactic, propionic and butyric acid produced by metabolism of microorganisms present in the food. The substrate concentration was set to 30 g COD/L on the basis of the concentration of carbohydrate because it was reported that carbohydrate has much higher hydrogen fermentation efficiency compared to other nutrients.

The pretreatment methods included heat treatment (90° C. for about 20 minutes), alkali treatment (pH 13 for about 24 hours) and acid treatment (pH 1 for about 24 hours). After adjusting the pH to pH 7, 200 mL of pretreated substrate was injected into an anaerobic batch bottle with a total volume of 635 mL.

The rectangular water tank made of iron was installed on an agitator. The batch bottles were placed in the rectangular water tank and a water circulator attached with a heater was connected to the rectangular water tank to maintain the temperature during fermentation at 35±1° C.

The agitation speed was controlled to about 100 rpm by using a magnetic bar in the batch bottle. The pH was prevented from being decreased by the production of organic acids during fermentation by using a pH sensor attached to the upper part of the batch bottle, and maintaining the pH at pH 5.0±0.2 by injecting 3N KOH.

The amount of hydrogen produced, hydrogen yield and carbohydrate removed under all pretreatment conditions are shown in Table 1. The hydrogen production was measured by using a syringe measuring gas amount and a gas chromatography.

TABLE 1

Amount of hydrogen produced, hydrogen yield and carbohydrate removed under each of the pretreatment methods.

| Pretreatment condition | Amount of produced hydrogen (mL) | Hydrogen yield per added carbohydrate (mol $H_2$/mol hexose$_{added}$) | Carbohydrate removal (%) | Hydrogen yield per consumed carbohydrate (mol $H_2$/mol hexose$_{consumed}$) |
|---|---|---|---|---|
| — | 48.96 | 0.07 | 83.09 | 0.08 |
| Heat | 888.84 | 1.27 | 88.45 | 1.44 |
| Alkali | 616.49 | 0.84 | 88.09 | 0.95 |
| Acid | 846.01 | 1.21 | 92.09 | 1.31 |

As shown in Table 1, there were no significant differences in the carbohydrate removal, but the treatments of heat, acid and alkali showed a respective decrease in hydrogen production efficiency. In the case of heat and acid treatments, hydrogen yields more than 1 mol on the basis of carbohydrate added and was generated in a considerably fast period (two or three days).

FIG. 1 is a graph showing the cumulative hydrogen production with time under various pretreatment conditions. Referring to FIG. 1, if an effective pretreatment is applied, food waste can function as both a substrate and an effective inoculum.

Figure 2:
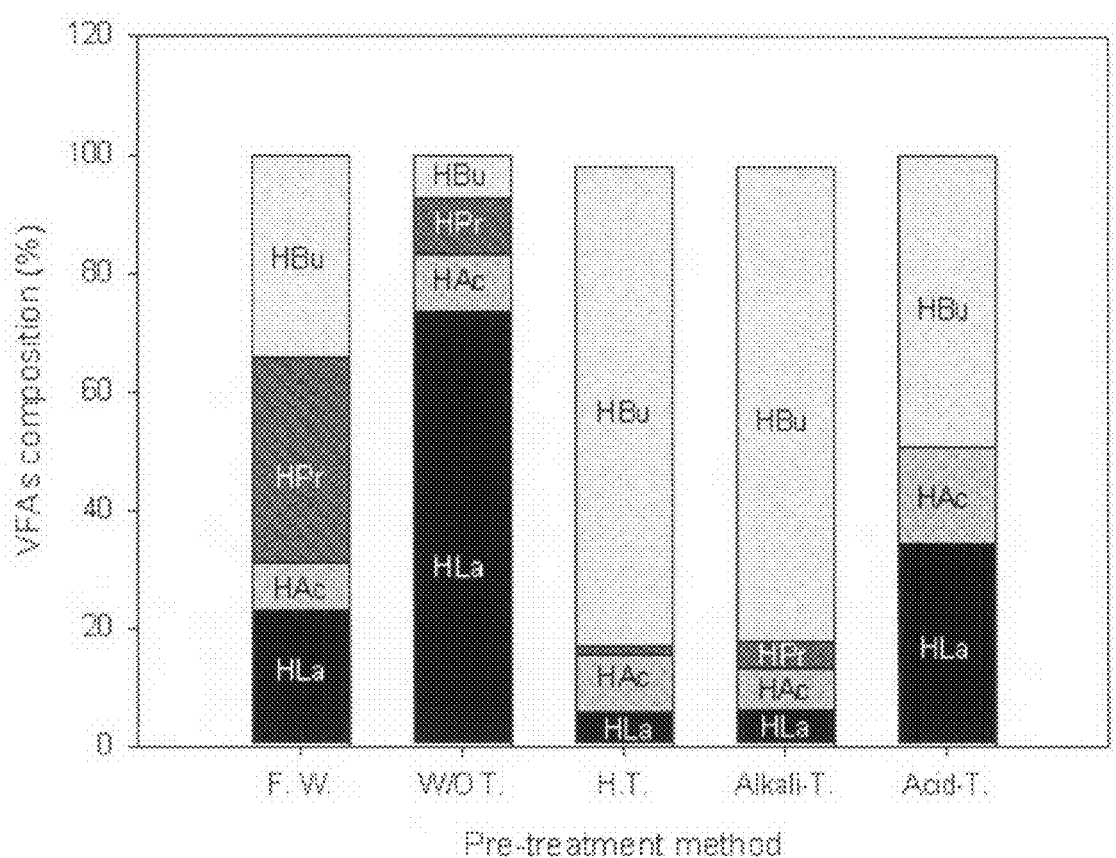
FIG. 2 is a graph representing the distribution of organic acids showing the effect of pretreatment.

The reason why the production of hydrogen is increased by pretreatment can be explained by the distribution of organic acids as shown in FIG. 2. In the case of omitting pretreatment, lactic acid (HLa) which was previously reported to be created without hydrogen production made up 70% or more of organic acids present. However, in cases where pretreatments were performed, the production of lactic acid was decreased while the production of butyric acid (HBu) related to hydrogen production was drastically increased. Furthermore, the production of propionic acid (HPr) occupying 30% or more in the food waste and known to consume hydrogen during its production was depressed by pretreatment The identification of microorganisms under each condition was performed by PCR-DGGE (Polymerase Chain Reaction-Denaturing Gradient Gel Electrophoresis) method and it was confirmed that microorganisms producing lactic acid and propionic acid were decreased through pretreatments (see "New Conceptual Hydrogen Fermentation Process Recovering Hydrogen from Food Waste" by Kim Dong-Hoon et al., Organic Resource Chemical Institute Symposium in Fall, 2006, p. 164-170).

Heat treatment was determined to be the optimum pretreatment in that the heat-treatment condition showed the highest hydrogen yield, in addition acid and alkali treatments have an economic burden, providing additional chemical materials and increasing pollutants.

Example 2

Example 2 addresses the effects of heat-treatment in more detail and identifies the optimum temperature for an economic treatment conditions. The heat-treatment temperatures were set to 60° C., 70° C., 80° C. and 90° C., and they were heated for 20 minutes, as in Example 1, and then placed into an anaerobic batch bottle. The conditions for controlling pH and other conditions were the same as Example 1.

Figure 3:
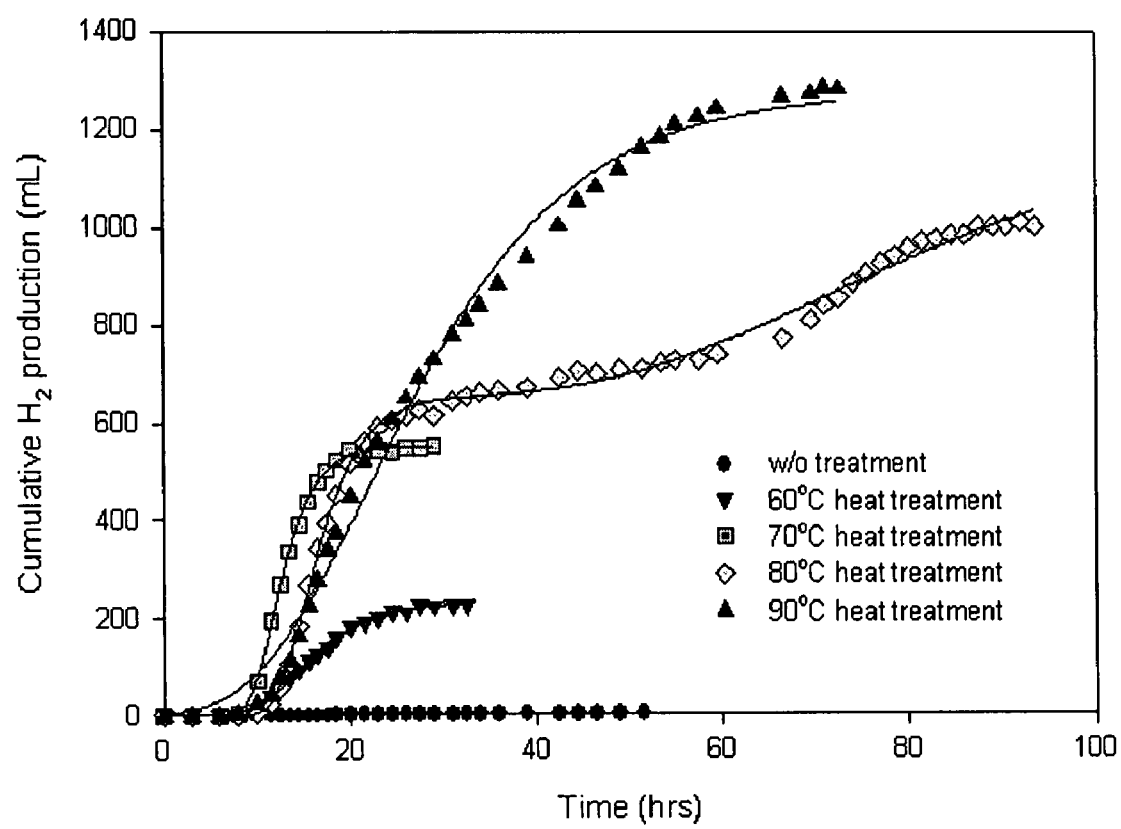
FIG. 3 is a graph showing the cumulative hydrogen production with time at various heat-treatment temperatures.
Figure 4:
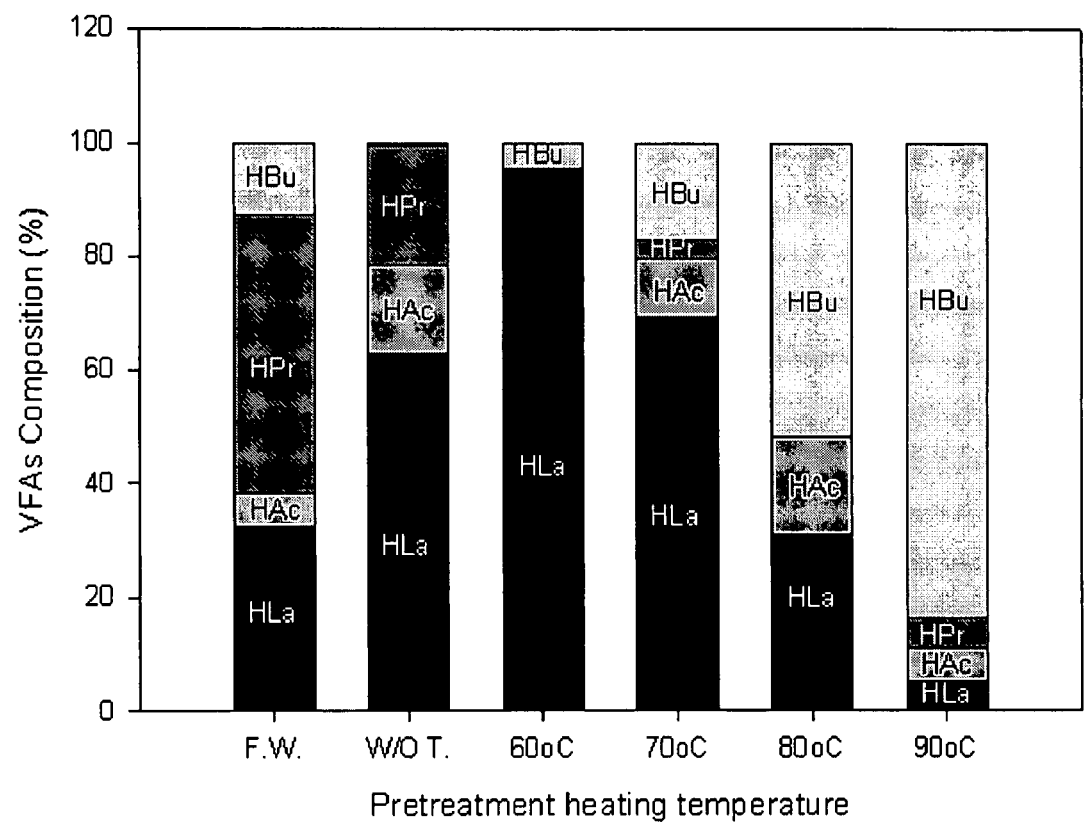
FIG. 4 is a graph showing the distribution of organic acids with temperature representing the effects of heat treatment temperature.

FIG. 3 is a graph showing cumulative hydrogen production with time under various pretreatment temperature conditions. Referring to FIG. 3, it was confirmed that hydrogen production increased with temperature. As known from the distribution of organic acids shown in FIG. 4, in cases that the pretreatment was not performed or performed at 60° C. and 70° C., the composition of lactic acid was present in a considerable quantity. However, in cases that a pretreatment was performed at above 80° C., the composition of lactic acid was drastically lowered, but that of butyric acid was increased. Additional analysis of microorganisms was not performed, but as indicated by the distribution of organic acids, it was suspected that the decease of lactic acid bacteria became the major reason for the successful hydrogen production at a higher temperature. In addition, the hydrogen yield at 90° C. was relatively high at 1.83 mol $H_2$/mol hexose$_{added}$ and the carbohydrate removal at this time was 92%.

Example 3

In order to find out the effects of initial pH first, 6 N KOH and HCl solution was injected to the food waste which was heated at 90° C. for 20 minutes to control the initial pH to pH 5, pH 6, pH 7, pH 8 and pH 9. The pH during fermentation was maintained at pH 5.0±0.2 by injecting 3 N KOH. The rate of decrease of pH was varied in accordance with initial pH but it was lowered below pH 5 after 7 hours to 15 hours. The properties of the food waste used in the present example are shown in Table 2. The values suggested were based on the concentration of carbohydrate of 30 g COD/L.

TABLE 2

Properties of the food waste used in Example 3

| Item | Unit | Value |
|---|---|---|
| COD | g COD/L | 59.0 |
| Carbohydrate | g COD/L | 30.0 |
| Total solid | g TS/L | 64.4 |
| Volatile solid | g VS/L | 61.2 |
| Ammonia | mg $NH_4$-N/L | 172.0 |
| pH | — | 4.7 |

Figure 5:
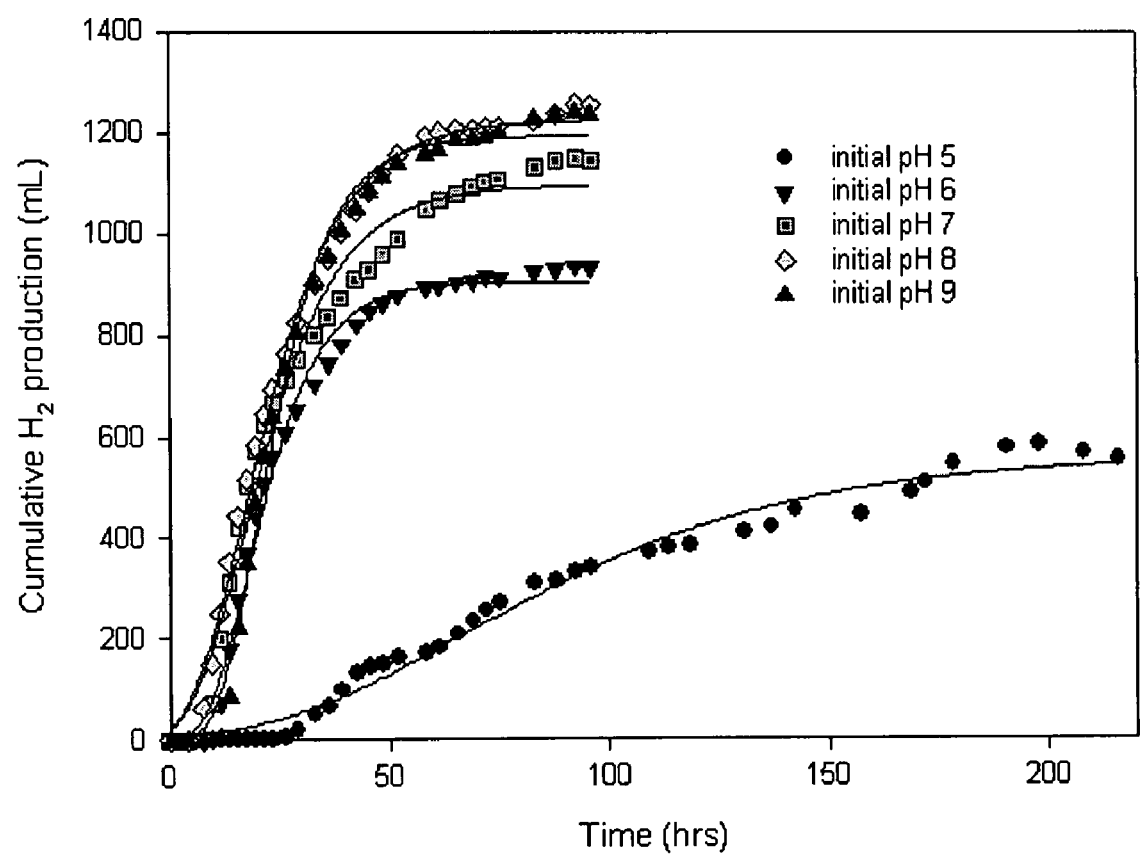
FIG. 5 is a graph showing the cumulative hydrogen production with time under various initial pH conditions when the heat-treated food waste was used.

FIG. 5 shows the cumulative hydrogen production with time at various initial pH. When the initial pH was high, the hydrogen production was successful, but it was apparent that hydrogen production was decreased at pH 5 and the speed of reaction was also drastically reduced.

As suggested in Table 3, carbohydrate removals were all similar at about 90% under any condition, but the hydrogen yield was the highest, at 1.79 mol $H_2$/mol hexose$_{added}$ at the initial pH of 8. The concentration of butyric acid was the highest at pH 8 while the concentrations of ethanol and propionic acid, which are not associated with the production of hydrogen, were relatively low in comparison with other initial pH.

Research to investigate the effect of initial pH at a fixed cultivation pH using organic waste as a substrate, has not yet been reported, however *Clostridium* sp. known as major hydrogen producing bacteria favors alcohol production at low or high pH (Refer to Jones and Woods, Microbiol. Rev., Vol. 50(4), 1986, p. 484-524).

In Table 3, the organic acid and ethanol were analyzed by using HPLC and Bio-LC respectively.

TABLE 3

Hydrogen production performance and organic acids analysis

| Initial pH | Amount of produced hydrogen (mL) | Carbohydrate removal (%) | Hydrogen yield per added carbohydrate (mol $H_2$/mol hexose$_{added}$) | Butyric acid concentration and composition (mg COD/L, %) | Ethanol concentration and composition (mg COD/L, %) | Propionic acid concentration and composition (mg COD/L, %) |
|---|---|---|---|---|---|---|
| 5 | 556 | 91.5 | 0.79 | 17,355 (41.9%) | 13,338 (32.2%) | 3,117 (7.5%) |
| 6 | 934 | 89.6 | 1.33 | 22,749 (56.5%) | 7,580 (18.8%) | 3,841 (9.5%) |
| 7 | 1,146 | 88.5 | 1.64 | 21,960 (55.1%) | 6,865 (17.2%) | 0 (0.0%) |
| 8 | 1,256 | 92.0 | 1.79 | 24,624 (60.6%) | 7,316 (18.0%) | 55 (0.2%) |
| 9 | 1,236 | 90.6 | 1.77 | 19,163 (54.4%) | 9,100 (25.8%) | 0 (0.0%) |

Example 4

After fixing the initial pH of heat-treated (90° C. for 20 min) food waste to pH 8, the pH during fermentation was maintained at pH 4.5±0.2, pH 5.0±0.2, pH 5.5±0.2, pH 6.0±0.2 and pH 6.5±0.2, respectively, to investigate the effects of cultivation pH. At this time, the control group where pH was not controlled was also observed. The properties of the food waste used in the present example are shown in Table 4, of which values were based on the carbohydrate concentration of 30 g COD/L, also.

TABLE 4

Properties of food waste used in Example 4.

| Item | Unit | Value |
|---|---|---|
| COD | g COD/L | 55.0 |
| Carbohydrate | g COD/L | 30.0 |
| Total solid | g TS/L | 57.1 |
| Volatile solid | g VS/L | 54.5 |
| Ammonia | mg $NH_4$-N/L | 224.0 |
| pH | — | 5.0 |

Figure 6:
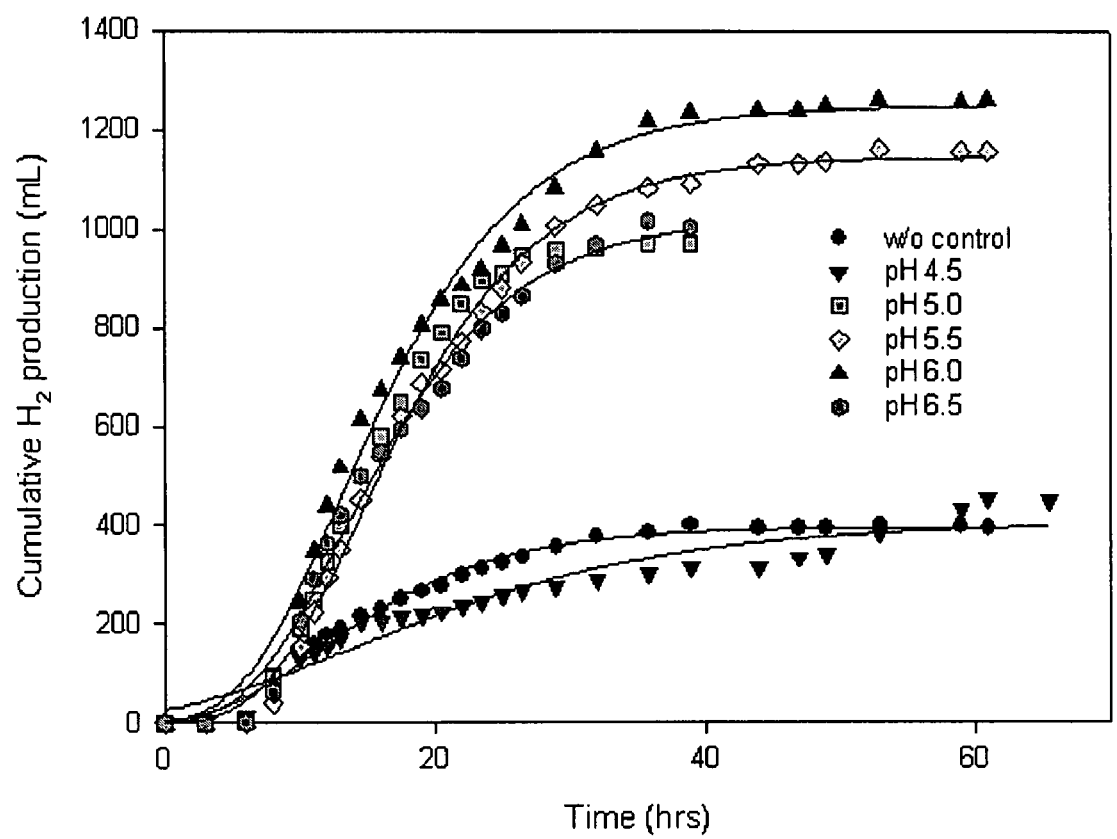
FIG. 6 is a graph showing the cumulative hydrogen production with time under various cultivation pH conditions where the heat-treated food waste was used and the initial pH was fixed to pH 8.

As shown from the cumulative hydrogen production presented in FIG. 6, when cultivation pH increased to 6, the amount of hydrogen produced continued to increase but decreased at pH 6.5. On the contrary, in case where the pH was 4.5 or was not controlled, the amount of hydrogen produced was drastically decreased. The hydrogen yield obtained at pH 6 was 1.80 mol $H_2$/mol hexose$_{added}$.

In conclusion, it is known that when food waste was heated at 90° C. for 20 minutes, and its concentration was set to 30 g Carbo. COD/L and the initial pH and the cultivation pH were controlled to 8 and 6, respectively (Examples 1 to 4) and the anaerobic state was maintained at 35° C., it was possible to produce hydrogen efficiently from the food waste within two or three days.

Example 5

In order to improve biodegradability and depress hydrogen consuming bacteria present in sewage sludge, the sludge was heated at 90° C. for 20 minutes as was the food waste. The components of the food waste and sewage sludge used in the present example are shown in the below Table 5.

TABLE 5

The components of food waste and sewage sludge

| Item | Unit | Food waste | Sewage sludge |
|---|---|---|---|
| Overall COD | g COD/L | 143.5 | 43.4 |
| Soluble COD | G COD/L | 54.8 | 10.6 |
| Total solid | g TS/L | 122.6 | 35.2 |
| Volatile solid | g VS/L | 121.1 | 24.2 |
| Carbohydrate | G COD/L | 84.4 | 4.0 |
| Protein | G COD/L | 23.3 | 9.9 |
| Ammonia | G $NH_4$-N/L | 0.3 | 0.2 |
| pH | — | 5.1 | 6.9 |

The concentration of carbohydrate included in sewage sludge was relatively low in comparison with the food waste and thus it was set to 30 g Carbo. COD/L on the basis of food waste and the sewage sludge was added by the volume corresponding to 0, 10, 20, 30 and 40% of that of the entire batch bottle.

In addition, in case that only sewage sludge was added without food waste injection, it was added by an amount corresponding to 40% of the entire batch bottle. An initial pH, a cultivation pH and a cultivation temperature of pH 8, pH 6 and 35° C., respectively, were selected, which were the optimum values obtained in the previous examples. Table 6 shows various concentrations depending on additions of sewage sludge and mixing ratios thereof.

TABLE 6

Various concentrations and mixing ratios depending on sewage sludge addition (%)

| Sewage sludge addition (%) | Based on mixing ratio (Food waste:sewage sludge) | | | Concentration | | |
|---|---|---|---|---|---|---|
| | carbohydrate | volatile solid | COD | carbohydrate | Organic solid | COD |
| 0 | 100:0 | 100:0 | 100:0 | 30.0 | 43.0 | 51.0 |
| 10 | 100:1.3 | 100:5.6 | 100:8.5 | 30.4 | 45.5 | 55.3 |
| 20 | 100:2.6 | 100:11.3 | 100:17.0 | 30.8 | 47.9 | 59.7 |
| 30 | 100:4.0 | 100:16.9 | 100:25.5 | 31.2 | 50.3 | 64.0 |
| 40 | 100:5.3 | 100:22.5 | 100:34.0 | 31.6 | 52.7 | 68.3 |
| 40 (only sewage sludge is added) | 0:100 | 0:100 | 0:100 | 1.6 | 9.7 | 17.4 |

Figure 7:
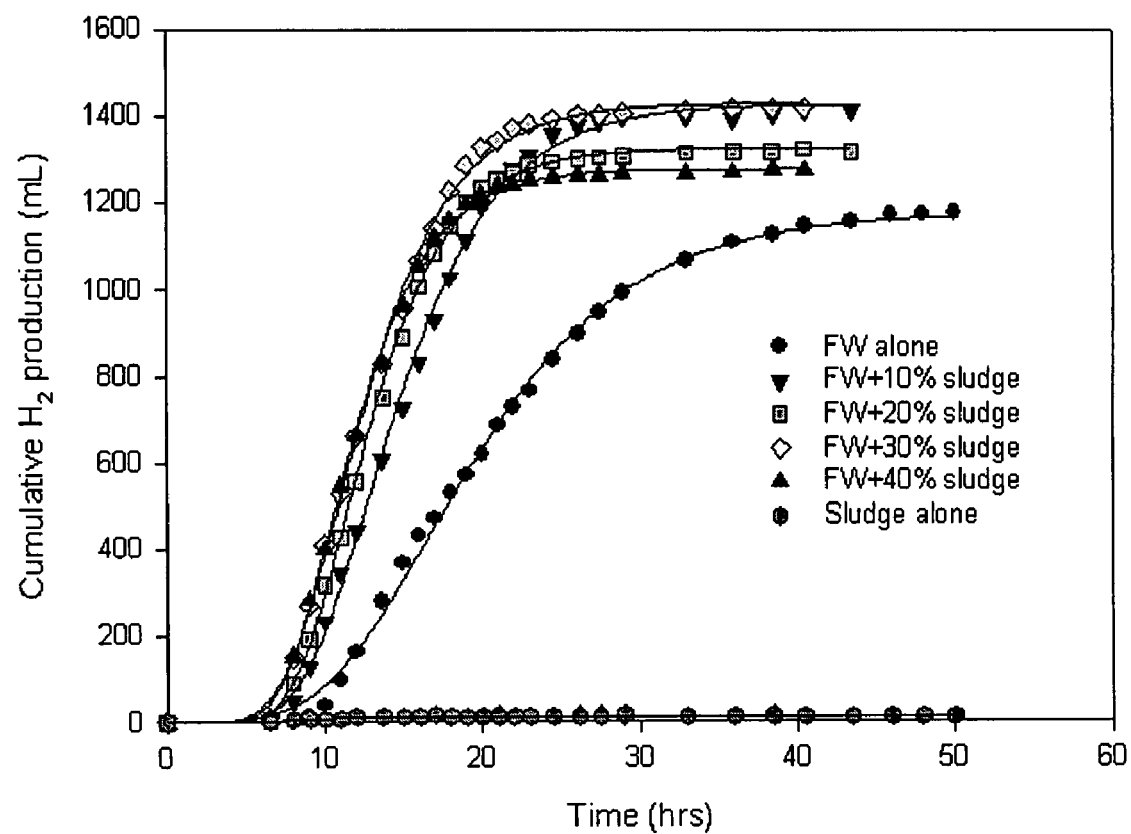
FIG. 7 is a graph showing the cumulative hydrogen production with time in accordance with the addition ratio in which the heat-treated sewage sludge was added to the heat-treated food waste.

FIG. 7 shows cumulative hydrogen production with time in accordance with the addition of varying percentages of sewage sludge added to the food waste. Hydrogen production was negligible in the case where only sewage sludge was added, which indicates that the process for producing hydrogen according to the present invention cannot be adopted for sewage sludge itself. It was obvious that the hydrogen production was higher in all cases where sewage sludge was mixed with food waste in comparison with the case where only food waste was used. Furthermore, in cases that sewage sludge was added, hydrogen production rate increased completing the production of hydrogen in two days.

In consideration that the existing continuous hydrogen fermentation process showed unstable hydrogen production performances and required a long start-up period and hydraulic retention time, it is clear that the process for the production of hydrogen according to the present invention can achieve stable hydrogen production from organic waste and further complete hydrogen fermentation within a shorter time.

Table 7 shows the hydrogen yield and carbohydrate removal under each condition. The carbohydrate removal was about 90% in all cases, which indicated that there was no inhibition for substrate degradation by sewage sludge addition.

In all the cases where sewage sludge was added, the hydrogen production and yield were increased. Especially, in case where 10% sewage sludge was added, the hydrogen yield based on volatile solid and COD was also higher in comparison to when only food waste was added.

The hydrogen yield based on carbohydrate and volatile solid was 1.99 mol $H_2$/mol hexose$_{added}$ and 155 mL/g $VS_{added}$, respectively, which was the highest level recorded in the world, hence representing the excellent performance of this invention.

TABLE 7

Hydrogen yield and carbohydrate removal under varying conditions.

| Adding rate of sewage sludge (%) | Hydrogen production (mL) | Carbohydrate removal (%) | Hydrogen yield | | |
|---|---|---|---|---|---|
| | | | Based on carbohydrate (mol $H_2$/mol hexose$_{added}$) | Based on volatile solid (mL $H_2$/g $VS_{added}$) | Based on COD (mL $H_2$/g $VS_{added}$) |
| 1 | 1,175 | 88.8 | 1.68 | 136 | 115 |
| 10 | 1,412 | 91.3 | 1.99 | 155 | 128 |
| 20 | 1,320 | 87.3 | 1.84 | 138 | 111 |
| 30 | 1,419 | 88.3 | 1.95 | 141 | 111 |
| 40 | 1,276 | 88.1 | 1.73 | 121 | 94 |
| 40 (only sewage sludge is added) | 13 | 90.5 | 0.35 | 7 | 4 |

Increase of hydrogen yield and production rate by sewage sludge addition might have come from nutrients present in the sewage sludge or metal components, which can be confirmed by further investigations analyzing atoms of each organic waste and additional batch experiments.

As described above, even if a hydrogen-producing inoculum is not further injected into the organic waste, the existing problem in the continuous process is that it only depends on the activity of microorganisms in the digester and can be solved by the pretreatment, such as heat-treatment, etc. of organic waste and anaerobic mesophilic-culture. In addition, this invention can reduce installing and operational cost by converting the conventional complex continuous process into a simple batch process. Therefore, it is possible to obtain an economic operation that does not require a long start-up period. Moreover, the method for producing hydrogen according to the present invention makes it possible to reduce the cost of transportation as a process capable of recovering hydrogen gas wherever organic waste is present.

In addition, according to the present invention, the addition of sewage sludge as a co-substrate is advantageous to treat organic waste with low biodegradability and to decrease the entire reaction time, which therefore decreases the required volume of the hydrogen fermentation tank, resulting in more economic operation.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A method for producing hydrogen from organic waste, comprising:
   (a) pretreating organic waste; and
   (b) fermenting the pretreated organic waste anaerobically, wherein the pretreated organic waste is a substrate and an inoculum,
   wherein the anaerobic fermentation is operated by batch process, and
   wherein the anaerobic fermentation has an initial pH of pH 7 to pH 9.

2. The method of claim 1, wherein the organic waste is selected from the group consisting of food waste, sewage sludge and livestock waste water, and combinations thereof.

3. The method of claim 1, wherein the pretreatment is selected from the group consisting of: a heat treatment, an acid treatment, an alkali treatment and combinations thereof.

4. The method of claim 3, wherein the heat treatment is for about 10 minutes to about 30 minutes at about 80° C. to about 100° C.

5. The method of claim 3, wherein the acid treatment is for about 12 hours to about 36 hours at pH 0.1 to pH 2.

6. The method of claim 3, wherein the alkali treatment is for about 12 hours to about 14 hours at about pH 12 to about pH 14.

7. The method of claim 1, wherein the anaerobic fermentation has a concentration of an initial substrate of about 25 g to about 35 g Carbo COD/L.

8. The method of claim 1, wherein the anaerobic fermentation occurs at a cultivation pH of about pH 5.6 to about pH 6.4.

9. The method of claim 1, wherein the anaerobic fermentation occurs at a cultivation temperature of about 33° C. to about 37° C.

10. The method of claim 1, further comprising adding a heat-treated sewage sludge to the pretreated organic waste as a supplemental substrate.

11. The method of claim 10, wherein the heat-treated sewage sludge is about 1% (v/v) to about 20% (v/v) of the volume of the entire reactor.

12. The method of claim 10, wherein the heat-treated sewage sludge is heated for about 10 minutes to about 30 minutes at about 80° C. to about 100° C.

13. The method of claim 1, wherein the anaerobic fermentation has an initial pH of about pH 7.5 to about pH 8.5.

* * * * *